United States Patent [19]

Kamen

[11] Patent Number: 4,816,019
[45] Date of Patent: Mar. 28, 1989

[54] INFILTRATION DETECTION SYSTEM USING PRESSURE MEASUREMENT

[76] Inventor: Dean L. Kamen, 46 Gage Rd., Bedford, N.H. 03102

[21] Appl. No.: 21,294

[22] Filed: Mar. 3, 1987

Related U.S. Application Data

[63] Continuation-in-part of Ser. No. 836,023, Mar. 4, 1986, Pat. No. 4,778,451.

[51] Int. Cl.$^4$ ............................................. A61M 31/00
[52] U.S. Cl. ........................................ 604/65; 604/131; 604/67; 604/1; 128/DIG. 13; 7/149
[58] Field of Search ................ 604/65, 902, 131, 141, 604/50, 118, 66, 67; 73/149; 128/DIG. 13

[56] References Cited

U.S. PATENT DOCUMENTS

| | | | |
|---|---|---|---|
| 2,116,636 | 5/1938 | Neumann | 73/149 |
| 2,747,740 | 5/1956 | Fatio | 73/149 |
| 3,618,602 | 11/1971 | Shaw | 604/50 |
| 3,901,231 | 8/1975 | Olson | 128/214 |
| 4,010,749 | 3/1977 | Shaw | 128/214 |
| 4,080,966 | 3/1978 | McNally | 128/214 |
| 4,332,246 | 6/1982 | Thomson | 128/214 |
| 4,378,808 | 4/1983 | Lichtenstein | 128/736 |
| 4,392,847 | 7/1983 | Whitney | 604/118 |
| 4,394,862 | 7/1983 | Shim | 604/67 |
| 4,395,259 | 7/1983 | Prestele | 604/67 |
| 4,448,204 | 5/1984 | Lichtenstein | 128/736 |
| 4,457,751 | 7/1984 | Rodler | 604/66 |
| 4,500,874 | 2/1985 | Jacobi et al. | 340/607 |
| 4,525,163 | 6/1985 | Slavik et al. | 604/65 |
| 4,526,574 | 7/1985 | Pekkarinen | 604/65 |
| 4,530,696 | 7/1984 | Bisera | 604/253 |
| 4,534,756 | 8/1985 | Nelson | 604/50 |
| 4,553,958 | 11/1985 | LeCocq | 604/67 |
| 4,634,430 | 1/1987 | Polaschegg | 604/141 |
| 4,648,869 | 3/1987 | Bobo | 604/49 |
| 4,710,163 | 12/1987 | Butterfield | 604/65 |

FOREIGN PATENT DOCUMENTS

| | | | |
|---|---|---|---|
| 0121931 | 10/1984 | European Pat. Off. | 604/131 |
| 1949616 | 4/1971 | Fed. Rep. of Germany. | |

Primary Examiner—C. Fred Rosenbaum
Assistant Examiner—Colleen M. Reilly
Attorney, Agent, or Firm—Bruce D. Sunstein; Mary R. Jankousky

[57] ABSTRACT

A system is provided for detecting the presence of an infiltration condition in a line delivering fluid to a patient. Stepping means subjects the fluid in the line to a negative pressure step. The pressure of the fluid is monitored, and processing means then determines whether an infiltration condition is present by determining whether the function of line pressure over time in response to the occurrence of a negative pressure step exhibits a relative slow return to the pre-step pressure, such relatively slow return being characteristic of the presence of infiltration.

18 Claims, 3 Drawing Sheets

INFILTRATION DETECTION SYSTEM USING PRESSURE MEASUREMENT

This is a continuation-in-part of copending application Ser. No. 836,023, filed on Mar. 4, 1986, now U.S. Pat. No. 4,778,451.

FIELD OF INVENTION

The present invention relates to systems for detecting the presence of infiltration of fluid being delivered through a line to a patient.

BACKGROUND ART

Numerous devices exist in the prior art for detecting infiltration, that is, a condition when an infusion needle has become dislocated from a patient's vein, and fluid being delivered enters surrounding tissue instead of the vein. Many of these devices, including the device disclosed in U.S. Pat. No. 4,530,696, examine the pressure of the fluid being delivered, and subject to processing the pressure data in order to determine the rate of change of pressure under certain circumstances. The inventor is unaware, however, of any system utilizing an external device for delivering to the fluid line a negative pressure step, the response to which is monitored by a pressure-sensitive device.

DISCLOSURE OF INVENTION

A system is provided for detecting the presence of infiltration of fluid being delivered through a line to a patient. The system includes an arrangement for subjecting the fluid in the line to a negative pressure step. The system monitors fluid pressure in the line, and determines whether the function of line pressure over time in response to the occurrence of a negative pressure step exhibits a relatively slow return to the pre-step pressure, the relatively slow return being characteristic of the presence of infiltration.

BRIEF DESCRIPTION OF THE DRAWINGS

The foregoing objects and features of the invention are better understood with reference to the following description taken with the accompanying drawings in which.

DETAILED DESCRIPTION OF SPECIFIC EMBODIMENTS

Figure 1:
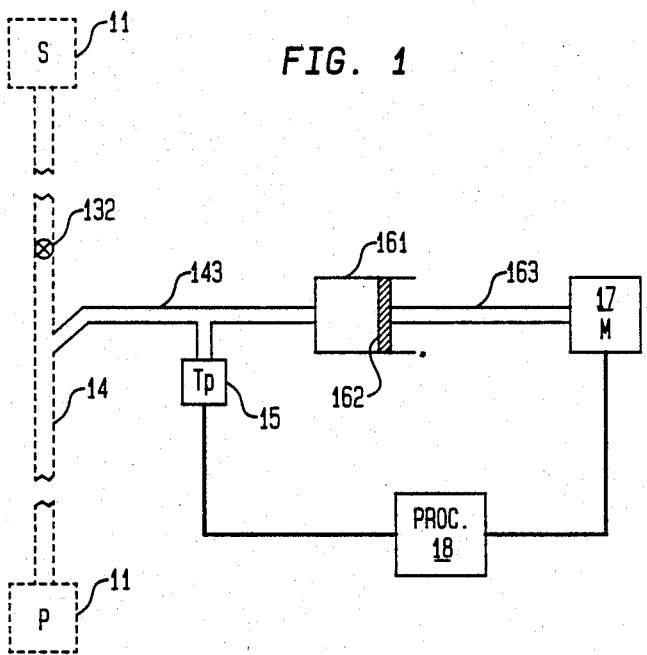
FIG. 1 is a simplified schematic of a first preferred embodiment of the invention.

FIG. 1 illustrates a preferred embodiment of an infiltration detection system in accordance with the present invention. It may typically be used in any instance wherein fluid from a delivery source 11 flows through a fluid line 14 to a patient 12. A line 143 is in pressure communication with the fluid line 14. Pressure in the fluid line 14 and the line 143 is monitored by pressure transducer 15. An arrangement such as piston 162 disposed in a cylinder is used for increasing or decreasing pressure in the line 14. Since infiltration is a condition being identified in relation to the flow of fluid into the patient 12, it is important that the effects of pressure in the line 14 be isolated from fluid delivery source 11. Such isolation may occur naturally if the source includes a pump that happens to be turned off, or a valve that is closed or substantially closed. In instances where the isolation is not inherently achieved, it may be achieved by providing in the fluid line a valve 132 that is kept closed during operation of the system described herein.

In operation, the piston 162, via piston rod 163 and motor 17 is quickly moved to the right to enlarge the volume 161 in the cylinder, thereby causing a negative pressure step to occur in line 14. The motor may, for example, be coupled to the piston rod with a conventional rack and pinion drive. Numerous other equivalent devices may be substituted, including a motor-driven bellows arrangement, a solenoid-operated diaphragm in an enclosure, or the like. The motor is activated, and the pressure transducer 15 output is monitored, by the processor 18.

Figure 2:
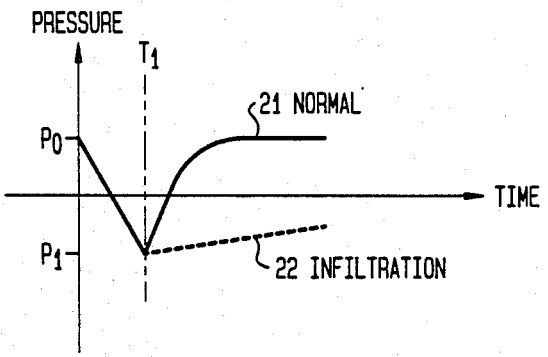
FIGS. 2 and 3 are pressure versus time graphs that illustrate operation of the embodiment of FIG. 1.

FIG. 2 illustrates pressure transducer 15 output in relation to the negative pressure step. Initially, there may be some positive pressure in the line 14. However, as the piston 162 moves to the right, the pressure decreases and goes negative to pressure $P_1$. Thereafter, if the infusion needle is situated in a vein of the patient, the effect will be to withdraw an incremental amount of blood from the patient, causing the pressure curve 21 to tend towards the initial pressure $P_0$. However, I have found that in the presence of infiltration, negative pressure at the site of the tip of the infusion needle in the patient will be unable to suck fluid into the system at the same rate as when the needle is properly situated in a vein, and, as indicated by curve 22, the rate of return of line pressure to the original pressure $P_0$ is dramatically slower than in the case of a non-infiltration mode. Accordingly, the processor 18 may monitor the rate of return and enter an alarm state in the event that the return is relatively slow.

In order to enhance the reliability of the determination, the embodiment of FIG. 1 may be used to induce additionally, for comparison purposes, a positive pressure step in the fluid line 14. The positive pressure step is induced in a fashion analogous to the negative pressure step discussed above. Thus, the piston 162 is moved to the left to reduce the volume 161 in the cylinder. It will often be convenient to induce the positive pressure step first, for reasons that will become apparent.

Figure 3:
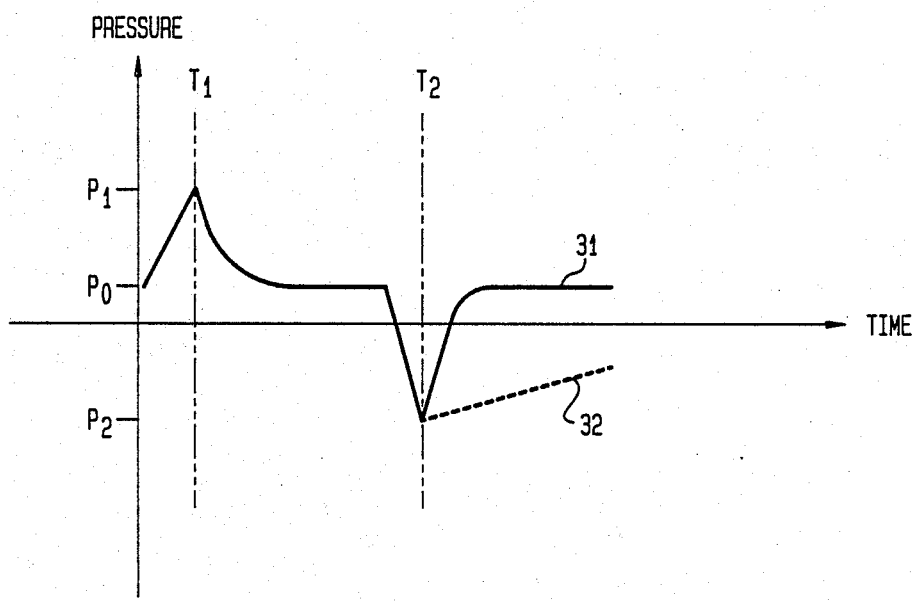

Referring to FIG. 3, the effects of delivering first a positive pressure step and then a negative pressure step are illustrated. At time $T_1$, following delivery of the positive pressure step, the pressure has risen from $P_0$ to $P_1$. As fluid profuses from the infusion needle site, the pressure will tend to return to the pre-step pressure $P_0$ at some rate. (Typically the pressure decay is exponential in nature, and any of a variety of techniques well known in the art may be used to analyze the decay function.) At time $T_2$, the negative pressure step has been delivered, causing the pressure to drop to value $P_2$. Thereafter, as discussed in connection with FIG. 2, in the absence of infiltration the pressure will again tend to return to the initial value $P_0$ and will follow curve 31. In the presence of infiltration, as discussed in connection with FIG. 2, the rate at which the pressure tends to return to the pre-step pressure is dramatically slower, as indicated by curve 32.

Accordingly, a preferred embodiment of my invention examines the response at times $T_1$ and $T_2$ respectively to the effects of positive and negative pressure steps to which the fluid line has been subjected. Infiltration is detected by identifying a substantial lack of symmetry in these two responses. One simple way of identifying a lack of symmetry is to determine, with respect to the response to the positive pressure step, the duration of time necessary for the pressure to drop, say, one-third of the distance between $P_1$ and $P_0$. Then, on the presence of the negative pressure step, the system can determine the duration necessary for the pressure to rise one-third of the distance between $P_2$ and $P_0$. The choice of one-third is, of course, arbitrary. A wide range of suitable fractions may be selected. Furthermore, in the presence of infiltration, the pressure may possibly never rise to $P_0$, in which case it is convenient to impose a maximum time limit for observing the response to the negative pressure step.

It will be apparent that the spacing between the positive pressure step, which serves as a reference, and the ensuing negative pressure step need only be sufficiently large as to permit measurement of the system response. Thus, a spacing of one to two seconds is more than ample in many applications. It will also be apparent that the detection system can be operated repeatedly over the course of delivery of fluid through the line to the patient. In fact, the system preferably should be operated on a periodic basis during infusion to insure that there is no infiltration during the entire course of infusion.

Figure 4:
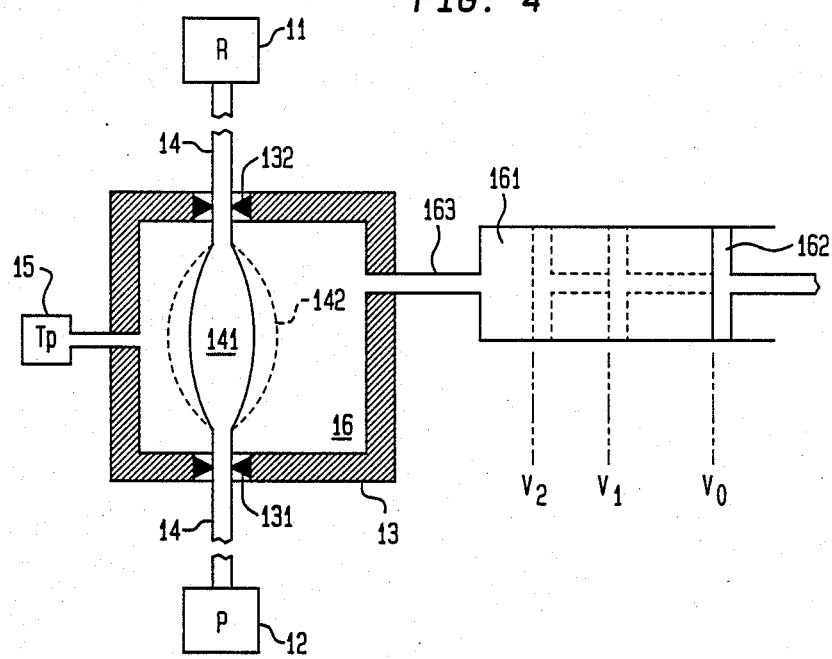
FIG. 4 is a second preferred embodiment of the invention.

The present invention may be incorporated in a fluid control system of the type disclosed in my International Application under the Patent Cooperation Treaty, and substantially similar U.S. application, each for a Pressure-Measurement Flow Control System, and each of which has been filed on the same day as the present application, and is hereby incorporated herein by reference. Although all embodiments disclosed in that application may be used for the purposes of the present invention, a representative embodiment thereof is illustrated in FIG. 4 herein. FIG. 4 shows first and second valve, 132 and 131, disposed in a fluid line 14 respectively above and below a chamber 16, having variable volume and a good seal from atmospheric pressure, through which runs a region 141 of the line that has a flexible wall to permit the line pressure to be communicated to the chamber pressure, which is measured via transducer 15. The volume is made variable by piston 162 in the illustrated cylinder.

With respect to FIG. 4, the present invention is applicable when upper valve 132 between the chamber 16 and the reservoir 11 is kept closed, and the lower valve 131 between the chamber 16 and the patient 12 is kept open. In this manner, displacement of the piston 162 can cause a concomitant increase or decrease in air pressure in the chamber 16, which, owing to the flexible walls in region 141, is communicated to the line. Accordingly, a positive or negative step to line pressure can be effectuated by movement of piston 162 in FIG. 4 in precisely the same fashion as discussed above in connection with FIG. 1. Consequently, an infiltration detection cycle may be commenced on a periodic basis using the device of FIG. 4 at any suitable time in the course of its operation, by closing upper valve 132, opening valve 131 and suitable actuation of the piston 162 while pressure is monitored by transducer 15. It will be noted that valve 132 is closed and valve 131 is open in the normal course of infusion of fluid into the patient using a device such as that of FIG. 4, so that no great inconvenience results when the infiltration cycle is commenced, and the cycle can be commenced at the conclusion of every infusion pump cycle or of any desired number of infusion pump cycles.

The design of FIG. 4 can readily be accommodated to permit infiltration detection even when used in conjunction with another type of infusion system. For such an application, P, item 12, may represent a junction with the fluid line of an existing infusion system, the lower valve 131 is always kept open, R (item 11) should be disregarded, and the upper valve 132 is always kept closed so that region 141 is effectively a cul-de-sac, the only opening of which is via line 14 to the junction 12.

The key features of the embodiment of FIG. 4 are simply that there is a region 141 in pressure communication with the fluid line; a housing 13 that houses auxiliary fluid (here, air) in communication with the region in such a way that a change in line pressure causes a corresponding change in auxiliary fluid pressure and vise-versa; a device 15 for measuring pressure of the fluid line; and finally, an arrangement 162 for displacing a predetermined volume increment of auxiliary fluid in such a manner that the predetermined volume increment causes a change in the auxiliary fluid pressure.

Figure 5:
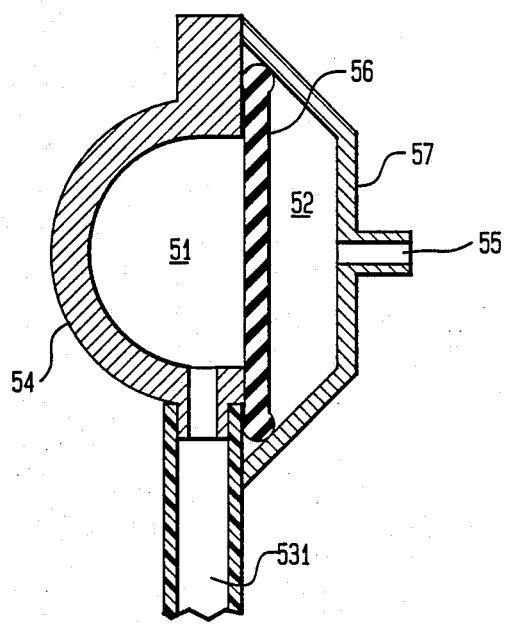
FIG. 5 is a further preferred embodiment that may be substituted for a portion of the structure shown in FIG. 4.

FIG. 5 illustrates an alternative embodiment for the housing 13 and related items. In this figure, region 51 is in pressure communication via line 531 with the fluid line to the patient. The region 51 is bounded by rigid enclosure 54 that is hemispherical in shape, sealed by flexible diaphragm 56, which separates region 51 from the balance of the enclosure 52, wherein air or other auxiliary fluid is permitted to enter via opening 55. Opening 55 may be connected via a line such as that shown as item 163 in FIG. 4 to a suitable cylinder piston arrangement indicated as item 162 in FIG. 4. A pressure transducer such as shown as item 15 in FIG. 4 may be located in any suitable location in FIG. 5, for example, via a Y-junction with the line connecting to opening 55. Opening 55 is disposed in rigid housing 57, so that the total volume of regions 52 and 51 in combination is constant. Owing to the flexibility of the diaphragm 56, the pressure in region 52 is substantially the same as that in region 51, just as, in the case of FIG. 4, the pressure in region 141 is substantially identical to that in the balance of enclosure 16.

What is claimed is:

1. A system for detecting the presence of infiltration of fluid being delivered through a line to a patient, the system comprising:

stepping means for subjecting the fluid in the line to a negative pressure step;

pressure monitoring means for monitoring fluid pressure in the line; and processing means, in communication with the pressure monitoring means and the stepping means, for actuating the stepping means and for determining whether the function of line pressure over time in response to the occurrence of a negative pressure step exhibits a markedly slow return to the pre-step pressure, such markedly slow return being characteristic of the presence of infiltration.

2. A system according to claim 1, wherein the processing means includes means (i) for determining the duration of time required for the line pressure to decrease in absolute value to a predetermined fraction of the absolute value of such pressure step, and (ii) for entering an alarm state in the event that the duration is substantially greater than a predetermined maximum limit.

3. A system according to claim 1, wherein
the stepping means includes means for subjecting the fluid in the line to a pressure step that may be selectably either positive or negative; and
the processing means includes means for identifying whether the function of line pressure over time in response to the occurrence of a negative pressure step is lacking in substantial symmetry with respect to the function of pressure over time in response to the occurrence of a positive pressure step.

4. A system according to claim 3, wherein the processing means includes means (i) for determining, in the event of either a positive or negative pressure step, the duration of time, up to a predetermined limit, required for the line pressure to decrease in absolute value to a predetermined fraction of the absolute value of such pressure step, (ii) for comparing the durations determined respectively for a positive and for a negative pressure step, and (iii) for entering an alarm state in the event that the duration for a negative pressure step is substantially greater than for a positive pressure step.

5. A system according to claim 1, wherein the stepping means includes:
a region in pressure communication with the line;
fluid housing means means for housing auxiliary fluid in communication with the region such that a change in line pressure causes a corresponding change in auxiliary fluid pressure and vice versa; and
displacement means for displacing a predetermined volume increment of auxiliary fluid, such that displacement of the predetermined volume increment causes a change in the auxiliary fluid pressure,
whereby the negative pressure step may be created by the displacement means.

6. A system according to claim 2, wherein the stepping means includes:
a region in pressure communication with the line;
auxiliary fluid housing means means for housing auxiliary fluid in communication with the region such that a change in line pressure causes a corresponding change in auxiliary fluid pressure and vice versa; and
displacement means for displacing a predetermined volume increment of auxiliary fluid, such that displacement of the predetermined volume increment causes a change in the auxiliary fluid pressure,
whereby the pressure step will be negative or positive according as the displacement means displaces a positive or negative volume increment of auxiliary fluid into the auxiliary fluid housing means.

7. A system according to claim 5, wherein
the auxiliary fluid housing means is disposed in relation to the region so as to define collectively therewith a fixed volume that is varied by the displacement means, and wherein the region includes a flexible interface surface defining a boundary with the auxiliary fluid.

8. A system according to claim 6, wherein
the auxiliary fluid housing means is disposed in relation to the region so as to define collectively therewith a fixed volume that is varied by the displacement means, and wherein the region includes a flexible interface surface defining a boundary with the auxiliary fluid.

9. A system according to claim 7, wherein
the region includes a substantially hemispherical rigid enclosure with an input and an output.

10. A system according to claim 8, wherein
the region includes a substantially hemispherical rigid enclosure with an input and an output.

11. A system according to claim 5, wherein
the processing means includes means (i) for determining the duration of time, up to a first predetermined limit, required for the line pressure to decrease in absolute value to a predetermined fractions of the absolute value of such pressure step, and (ii) for entering an alarm state in the event that the duration is substantially greater than a second predetermined limit.

12. A system according to claim 6, wherein
the processing means includes means (i) for determining, in the event of either a positive or negative pressure step, the duration of time, up to a predetermined limit, required for the line pressure to decrease in absolute value to a predetermined fraction of the absolute value of such pressure step, (ii) for comparing the durations determined respectively for a positive and for a negative pressure step, and (iii) for entering an alarm state in the event that the duration for a negative pressure step is substantially greater than for a positive pressure step.

13. A system according to claim 5, wherein the auxiliary fluid is air.

14. A system according to claim 6, wherein the auxiliary fluid is air.

15. A system according to claim 12, wherein the auxiliary fluid is air.

16. A system for detecting the presence of infiltration of fluid being delivered though a line to a patient, the system comprising:
a region in pressure communication with the line, such region having a flexible interface surface;
auxiliary fluid housing means, for housing auxiliary fluid, such means disposed in relation to the region so as to define collectively therewith a volume that is normally fixed, and wherein the interface surface is disposed to define a boundary with the auxiliary fluid;
displacement means for displacing a predetermined volume increment of auxiliary fluid, such that displacement of the predetermined volume increment causes a change in the normally fixed volume and in the auxiliary fluid pressure, so that the displacement means upon actuation will subject fluid in the line to a pressure step that may be negative or positive according as the volume increment in the fixed volume is positive or negative respectively; and
processing means (i) for determining, in the event of either a positive or negative pressure step, the duration of time, up to a predetermined limit, required for the line pressure to decrease in absolute value to a predetermined fraction of the absolute value of such pressure step, (ii) for comparing the durations determined respectively for a positive and for a negative pressure step, and (iii) for entering an alarm state in the event that the duration for a negative pressure step is substantially greater than for a positive pressure step.

17. A system according to claim 16, wherein the auxiliary fluid is air.

18. A system according to claim 16, further comprising:
means for actuating the displacement means and the processing means repetitively in the course of delivery of fluid through the line.

* * * * *